United States Patent [19]

Saji et al.

[11] Patent Number: 4,739,060
[45] Date of Patent: Apr. 19, 1988

[54] RADIOACTIVE AND NON-RADIOACTIVE IODOBUTYROPHENONE DERIVATIVE

[75] Inventors: Hideo Saji, Uji; Iwoa Nakatsuka, Kobe; Masami Okuno, Osaka; Akira Yokoyama, Otsu, all of Japan

[73] Assignee: Sumitomo Chemical Company, Limited, Osaka, Japan

[21] Appl. No.: 896,197

[22] Filed: Aug. 14, 1986

[30] Foreign Application Priority Data

Aug. 26, 1985 [JP] Japan .................. 60-188274

[51] Int. Cl.$^4$ .......................... C07D 471/10
[52] U.S. Cl. ................................. 546/20
[58] Field of Search .................. 546/20; 514/278

[56] References Cited

U.S. PATENT DOCUMENTS

| | | | |
|---|---|---|---|
| 3,155,669 | 11/1964 | Janssen | 546/20 |
| 3,890,323 | 6/1975 | Yamamoto et al. | 544/230 |
| 3,979,390 | 9/1976 | Sasajima et al. | 544/230 |

FOREIGN PATENT DOCUMENTS

| | | | |
|---|---|---|---|
| 253507 | 4/1967 | Austria | 546/20 |
| 50-5385 | 1/1975 | Japan | 544/230 |
| 59-95288 | 6/1984 | Japan | 546/20 |
| 2155473 | 9/1985 | United Kingdom | 546/20 |

OTHER PUBLICATIONS

Glowinski et al., "J of Neurochemistry" (1966), vol. 13, pp. 655–669.

Primary Examiner—Robert T. Bond
Attorney, Agent, or Firm—Stevens, Davis, Miller & Mosher

[57] ABSTRACT

A radioactive or non-radioactive 2-iodobutyrophenone derivative the formula:

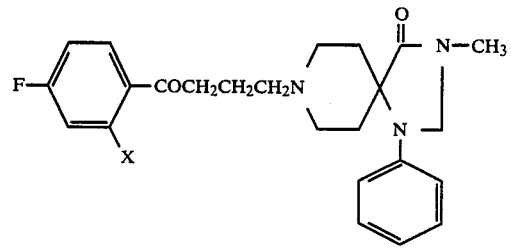

wherein X is a radioactive or non-radioactive iodine atom. The radioactive compound has a high affinity for dopamine receptors and is very useful as a radioactive diagnostic agent and as a radiopharmaceutical, and the non-radioactive compound also as a high affinity for dopamine receptors and is very useful as a neuroleptic, a sedative, an anodyne, a tranquilizer, etc.

5 Claims, No Drawings

RADIOACTIVE AND NON-RADIOACTIVE IODOBUTYROPHENONE DERIVATIVE

This invention relates to a novel radioactive or non-radioactive 2-iodobutyrophenone derivative of the formula:

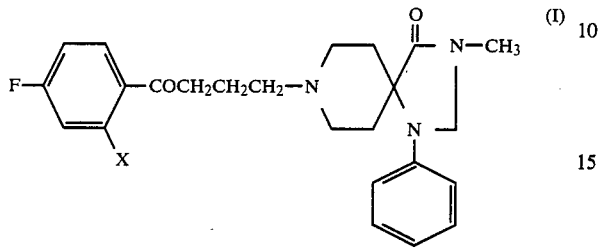

wherein X is a radioactive or non-radioactive iodine atom, and processes for producing the same.

The compound of this invention is a novel compound not disclosed in any literature. The radioactive compound of this invention has a high affinity for dopamine receptors as well as iodospiroperidol, which has been disclosed in Japanese Pat. Appln. Kokai (Laid-Open) No. 59-95288. However, in the biodistribution studies, the radioactive compound of this invention showed higher brain uptake (Factor: approximately 2.0) than that of radioactive iodospiroperidol. Therefore, the radioactive compound of this invention is very useful as a radioactive diagnostic agent and as a radiopharmaceutical.

The radioactive 2-iodobutyrophenone derivative (I) produced by this invention permits quantitative measurement of dopamine receptors in the living human brain by applying a suitable method such as a probe method, a single photon emission computed tomography (SPECT) method, and the like. Therefore, a certain neuropsychiatric disorder caused by abnormality of dopamine receptor concentration can be diagnosed by using above system. The radioactive compound of this invention can also be used as a standard material for evaluation in vivo of dopamine receptor specific drugs, and it is useful for the diagnosis and treatment of other diseases, such as breast cancer, resulting from a change of dopamine receptors. Furthermore, the radioactive compound of this invention can be used as a radioactive ligand in the various kinds of in vitro radioassays such as RIA, RRA and the like. On the other hand, since the non-radioactive 2-iodobutyrophenone derivative of this invention also has a high affinity for dopamine receptors and has a central nervous system depressing action, antiadrenaline action and the like, it is useful as a neuroleptic, a sedative, an anodyne, a tranquilizer, and the like.

The method of the preparation of the compound of this invention will be described below.

The compound of this invention of the above-mentioned formula (I) can be produced by a conventional method for the synthesis of radioactive or non-radioactive iodine compounds. For instance, it can be produced according to either Process A or Process B shown below.

PROCESS A

A 2-iodospiroperidol compound of the formula (II):

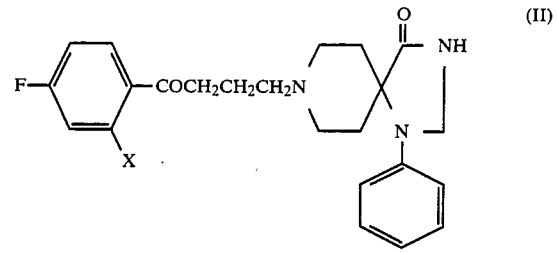

wherein X is the same as described above, which is disclosed in Japanese Pat. Appln. Kokai (Laid-Open) No. 59-95288 is reacted with methyl bromide or methyl iodide in a solvent, in the presence of a base, if necessary, in the presence of a crown-ether or a phase transfer catalyst, at a temperature in a range of 30° to 100° C. As the solvent described above, for example, acetone, methyl ethyl ketone, methylene chloride, dichloroethane, ether, isopropyl ether, tetrahydrofuran, dioxane, benzene, acetonitrile, water and a mixture of these solvents are exemplified. And as the base, for example, a caustic alkali, an alkali metal, an alkali metal hydride and a quaternary amine compound are exemplified.

PROCESS B

A halogeno compound of the formula:

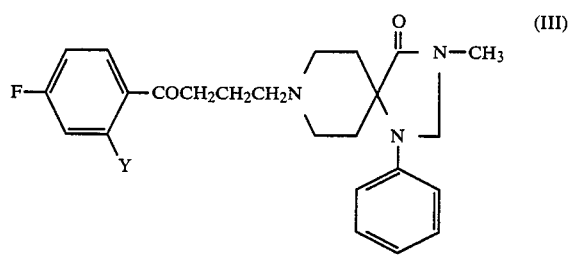

wherein Y is a halogen atom is subjected to an exchange reaction with a radioactive or non-radioactive iodine metal salt in a solvent at a temperature of 50° to 180° C. As the solvent described above, for example, acetonitrile, dimethylformamide, ethylene glycol, an ether derivative of ethylene glycol, an ether derivative of diethylene glycol, water and the like are exemplified.

The compound (I) obtained can be purified by a conventional method such as thin layer chromatography (TLC) or high-performance liquid chromatography (HPLC).

In the process of this invention, for example, I-123, I-125, I-131, I-132, etc. are exemplified as the radioactive iodine atom, and I-123 is preferred. The radioactive iodine metal salt means a metal salt of the above radioactive iodine, and may be any of those capable of providing a radioactive I$^-$ ion, though alkali metal salts such as, for example, sodium iodide, potassium iodide and lithium iodide are preferred. As the halogen ion in the formula (III), anions of chlorine, bromine, iodine and the like are exemplified.

The present invention will further be specifically described below referring to Examples.

EXAMPLE 1

Preparation of 8-[4-(4-fluoro-2-iodophenyl)-4-oxobutyl]-3-methyl-1-phenyl-1,3,8-triazaspiro[4.5]decan-4-one (2-iodomethylspiroperidol).

Methylene chloride (10 ml), methyl iodide (62 μl) and tetra-n-butylammonium hydroxide (5 ml) were added to 2-iodospiroperidol (260 mg), and the mixture was stirred at a temperature of 40° to 50° C. for thirty minutes. After cooling, water is added to the reaction mixture and the mixture was subjected to an extraction by methylene chloride. Then the solvent was removed by distillation to obtain a crude product. This was purified by silica gel column chromatography to obtain 2-iodomethylspiroperidol (107 mg).

Melting point: 115°–118° C.
IR(CHCl$_3$)cm$^{-1}$: 1705 (C=O).
$^1$H-NMR(CDCl$_3$) δ (ppm): 1.60–3.10 (14H, m, —CH$_2$—), 3.00 (3H, s, CH$_3$), 4.70 (2H, s,

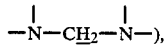

6.80–8.00 (8H, m, benzene ring H).
Mass spectrum (70 eV) m/e: $\overline{535}$ [M+].

EXAMPLE 2

Preparation of [$^{125}$I]-8-[4-(4-fluoro-2-iodophenyl)-4-oxobutyl]-3-methyl-1-phenyl-1,3,8-triazaspiro[4.5]decan-4-one ([$^{125}$I]-2-iodomethylspiroperidol).

Methylene chloride (500 μl), methyl iodide (10 μl) and tetra-n-butylammonium hydroxide (60 μl) were added to an aqueous solution of [$^{125}$I]-2-iodospiroperidol (300 μl, 500 μCi). The mixture was stirred at room temperature for thirty minutes. A methylene chloride layer was separated, dried and concentrated under reduced pressure. The resulting crude product was purified by HPLC (column; Licrosorb® RP-18, solvent: water/methanol/acetonitrile/triethylamine=164/336/68/0.2 to obtain [$^{125}$I]-2-iodomethylspiroperidol 400 μCi). This product was identical with the specimen obtained in the Example 1 in Rf values of TLC and HPLC.

EXAMPLE 3

Preparation of [$^{125}$I]-2-iodomethylspiroperidol by exchange method.

Dimethylformamide (10 μl) and Na$^{125}$I (2 mCi) were added to 2-iodomethylspiroperidol (5 μg) synthesized in the Example 1, and a slight amount of 0.1N sulfuric acid was further added thereto, and the resulting mixture was heated at 100° C. for 3 hours. After cooling, the resulting crude product was purified by HPLC to obtain [$^{125}$I]-2-iodomethylspiroperidol (0.75 mCi). This product was identical with the specimen obtained in Example 1 in Rf values of TLC and HPLC.

We claim:

1. A radioactive or non-radioactive 2-iodobutyrophenone derivative of the formula:

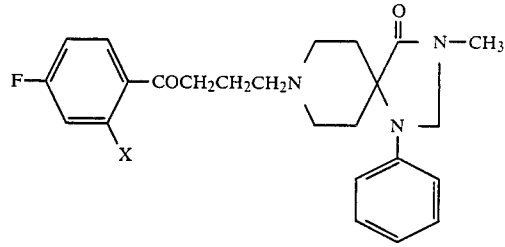

wherein X is a radioactive or non-radioactive iodine atom.

2. The 2-iodobutyrophenone derivative according to claim 1, wherein X is an atom selected from the group of iodine isomers consisting of I-127, I-123, I-125, I-131 and I-132.

3. A radioactive 2-iodobutyrophenone derivative of the formula:

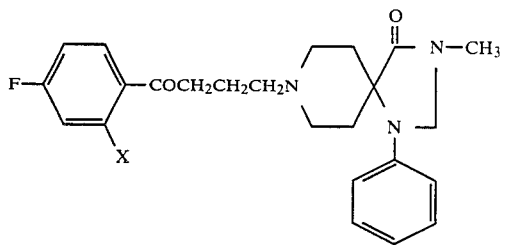

wherein X is a radioactive iodine atom.

4. The 2-iodobutyrophenone derivative according to claim 3, wherein X is an atom selected from the group of iodine isomers consisting of I-123, I-125, I-131 and I-132.

5. The 2-iodobutyrophenone derivative according to claim 4, wherein X is I-125.

* * * * *